(12) United States Patent
Cha

(10) Patent No.: US 7,641,874 B2
(45) Date of Patent: Jan. 5, 2010

(54) MICROWAVE INDUCED DESTRUCTION OF IMPURITIES FROM BIOGAS AND NITROGEN OXIDES FROM ENGINE EXHAUST

(75) Inventor: Chang Yul Cha, Laramie, WY (US)

(73) Assignee: CHA Corporation, Laramie, WY (US)

( * ) Notice: Subject to any disclaimer, the term of this patent is extended or adjusted under 35 U.S.C. 154(b) by 166 days.

(21) Appl. No.: 12/013,870

(22) Filed: Jan. 14, 2008

(65) Prior Publication Data

US 2008/0197013 A1    Aug. 21, 2008

Related U.S. Application Data

(60) Provisional application No. 60/884,985, filed on Jan. 15, 2007.

(51) Int. Cl.
*A62D 3/178* (2007.01)
*B01D 53/52* (2006.01)
*B01D 53/56* (2006.01)
*B01D 53/92* (2006.01)
*C01B 17/04* (2006.01)

(52) U.S. Cl. .................. 423/212; 423/235; 423/573.1; 502/20; 502/56; 502/416; 502/439; 502/514; 204/157.3; 204/157.43; 204/157.46; 204/157.49

(58) Field of Classification Search ............. 423/212, 423/235, 573.1; 502/20, 56, 416, 439, 514; 204/157.3, 157.43, 157.46, 157.49
See application file for complete search history.

(56) References Cited

U.S. PATENT DOCUMENTS

| 4,314,977 | A | * | 2/1982 | Kulik .................... 423/235 |
| 5,152,970 | A | | 10/1992 | van der Wal et al. |
| 5,246,554 | A | | 9/1993 | Cha |
| 5,256,265 | A | | 10/1993 | Cha |
| 5,269,892 | A | | 12/1993 | Cha |
| 5,362,451 | A | | 11/1994 | Cha |
| 5,536,477 | A | | 7/1996 | Cha et al. |
| 5,589,599 | A | | 12/1996 | McMullen et al. |
| 5,767,470 | A | | 6/1998 | Cha |

(Continued)

OTHER PUBLICATIONS

Slowe, Jon, Biogas, A Growing Niche for Distributed Generation, E Source, DE-21. May 2003.

(Continued)

*Primary Examiner*—Timothy C Vanoy
(74) *Attorney, Agent, or Firm*—John P. O'Banion

(57) ABSTRACT

Granulated Activated Carbon (GAC) is used to remove hydrogen sulfide ($H_2S$) from the biogas produced in an anaerobic digester. The cleaned biogas is then combusted in a reciprocating engine. The exhaust of the engine is passed through a heat exchanger and then through GAC in an adsorber to adsorb nitrogen oxides (NOx) and any sulfur oxides (SOx). The GACs containing NOx, $H_2S$, and SOx, are transported to a microwave reactor, mixed, and exposed to microwave energy. The $H_2S$ and NOx are desorbed from the GAC and chemically combined to produce nitrogen, carbon dioxide, sulfur and water. Unreacted nitrogen oxides or hydrogen sulfide are transported to a second reactor containing carbon media to be reacted by a further microwave process. Sulfur is removed with a filter as a solid and the remaining inert components are vented to the atmosphere. The GAC is regenerated and reused to remove additional $H_2S$ and NOx.

10 Claims, 3 Drawing Sheets

U.S. PATENT DOCUMENTS

| | | | |
|---|---|---|---|
| 6,027,698 | A | 2/2000 | Cha |
| 6,207,023 | B1 | 3/2001 | Cha |
| 6,284,202 | B1 | 9/2001 | Cha et al. |
| 6,419,799 | B1 | 7/2002 | Cha |
| 6,592,723 | B2 | 7/2003 | Cha |
| 6,783,632 | B2 | 8/2004 | Cha |
| 6,830,662 | B2 | 12/2004 | Cha |
| 2006/0000352 | A1 | 1/2006 | Tower et al. |
| 2007/0126649 | A1 | 6/2007 | Cha et al. |

OTHER PUBLICATIONS

Cha Cy, Microwave Technology for Superfund Site Remediation, NIEHS Project Brief, Jul. 2003.

Zicari Steve, Removal of Hydrogen Sulfide From Biogas Using Cow-Manure Compost, Thesis at Cornell University, Jan. 2003, 132 pages.

California Expands its Role in Renewable Energy Development, California Biomass Collaborative Newsletter, UC Davis, California, vol. 2, No. 1, Winter 2005.

Cha, Cy, Prototype Demonstration of CHA NOx Removal System for Treatment of Stationary Diesel Exhaust, Final Report, California Air Resources Board, Aug. 1998.

Greenhouse Gas Technology Center, Environmental Technology Verification Report, Swine Waste Electric Power and Heat Production—Martin Machinery Internal Combustion Engine, US EPA, SRI/USEPA-GHG-VR-22, Sep. 2004.

Lusk, P, Methane Recovery from Animal Manures The Current Opportunities Casebook, National Renewable Energy Laboratory, NREL/SR-580-25145, Sep. 1998.

* cited by examiner

MICROWAVE INDUCED DESTRUCTION OF IMPURITIES FROM BIOGAS AND NITROGEN OXIDES FROM ENGINE EXHAUST

CROSS-REFERENCE TO RELATED APPLICATIONS

This application claims priority from U.S. provisional application Ser. No. 60/884,985 filed on Jan. 15, 2007, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to removal of hydrogen sulfide ($H_2S$) in biogas and subsequent removal of Nitrogen oxides (NOx) in engine exhaust, and more particularly to treatment and removal of $H_2S$ and NOx in a biogas power system with carbon media and a microwave treatment system.

2. Description of Related Art

There are over 2100 dairies just in California with a potential to produce about 40 million cubic feet per day of biogas with a potential generation capacity of about 136-140 MW. Additionally, anaerobic digesters such as landfills and sewage and food digesters can produce biogas that can be used to make electricity, hot water or other uses. However, contaminants in the biogas limit the ability to fully develop these resources for electric generation such as fuel cells and turbines. Contaminants such as $H_2S$ in the biogas also prevent the use of post combustion technologies such as catalysts on engines.

Advanced technologies that could reliably reduce NOx emissions from small (50 kW to 400 kW) reciprocating engines and meet the California Air Resources Board (CARB) 2007 NOx standards for Combined Heat and Power (CHP) distributed generation systems have been researched. Hydrogen sulfide ($H_2S$) produced in the biogas causes significant equipment operation and maintenance issues and restricts power equipment options almost exclusively to reciprocating engines. Sulfur dioxide ($SO_2$) in the engine exhaust, even in small quantities, will poison catalytic emission control systems otherwise suitable for use on natural gas fired engines.

Two emission control strategies may meet the CARB 2007 NOx standards for reciprocating engines; combustion modifications and post combustion control. Lean burn engines use a high air to fuel ratio to lower combustion temperature and NOx formation. This combustion technology was developed for use on large natural gas engines and only recently has been offered on smaller engines. About ten reciprocating engine models below 400 kW are currently available with lean burn technology. Expected NOx emissions range from 0.7 to about 2 g/bhp-hr (without post combustion catalyst). Only four engine manufacturers are known to warrant NOx emissions on lean burn engines smaller than 400 kW fueled by biogas. Three manufacturers indicate that they would guarantee NOx emissions to 1.0 g/bhp-hr without a catalyst.

Five commercially available technologies for post combustion controls are possibilities for use on reciprocating engines burning biogas. These include Oxidation Catalyst, Non-selective Catalytic Reduction (NSCR), Selective Catalytic Reduction (SCR), Selective Non Catalytic Reduction (SNCR) and NOx adsorbents (SCONOX and NOXTECH). The Oxidation Catalyst is used with rich burn engines to remove VOC's and CO and does not remove NOx. The oxidation catalyst, NSCR and SCR are susceptible to Sulfur poisoning and would require reliable and efficient pretreatment of the biogas to remove $H_2S$. SNCR uses urea or ammonia to remove NOx but has not been used successfully on IC engines. SCONOX is a dry absorbent that removes NOx and must be regenerated, but was developed for turbines and has not been used on IC engines. The NOXTECH® system relies on the injection of urea or ammonia into the exhaust of an IC engine and reacts with NOx after heating the exhaust to between 1400-1500 degrees Fahrenheit. Additional fuel and chemicals are needed and the requirement to heat the exhaust complicates installation of heat recovery equipment on the engine exhaust. A small amount of ammonia slip is also reported. Expected NOx emissions for NOXTECH are at 0.3 to 0.5 g/bhp-hr (0.92 to 1.5 lb/MW-hr) which will not meet the 2007 CARB standard of 0.07 lb/MW-hr or the proposed 2008 standard of 0.7 lb/MW-hr for engines operating on digester biogas.

The cost to install and operate these post combustion technologies on small to medium reciprocating engines is significant. Equipment cost coupled with the uncertainty of performance running on biogas makes it difficult to recommend funding for projects without manufacturer assurance of meeting the proposed CARB standards for NOx. A survey of eight engines currently operating on dairy digesters in California shows that all are rich burn engines and that only two are equipped with SCR technology. Both the units with SCR report problems with the catalyst and $H_2S$ removal system.

Dairy digesters typically produce about 50%-60% methane, 40%-50% $CO_2$ and sulfur impurities mostly in the form of $H_2S$ in the range of 0.06% to 0.2%. Hydrogen Sulfide has a strong order that can be detected at threshold levels of about 0.47 ppb and has an OSHA IDLH level of 300 ppm. Assuming emissions of SOx are not an issue, boilers can tolerate $H_2S$, levels up to 1000 ppm, reciprocating engines about 10 to 100 ppm and fuel cells 10 ppm to 20 ppm.

Reciprocating engines operating on digester biogas compared to natural gas engines cost about 20% more to install and about 80% more to maintain. Sulfur plugs filters, causes deposits on valves and cylinders and contaminates lubricating oil. It has been reported that some operators must change spark plugs frequently ($1000 annually) and change oil as often as weekly ($350 to $1000 per month).

The $H_2S$ pretreatment system of choice for most dairy digesters is gas contact with an iron oxide media. The most well known treatment system is an iron sponge. This is a container of iron oxide impregnated media (typically woodchips) that scrubs the inlet gas from the digester. The iron sponge is sized for a residence time of about 60 seconds and the media can collect up to about 2.5 times its weight in sulfur compounds. The media can be partially regenerated by exposure to air or by wetting for about 10 days. Eventually the media must be discarded and replaced with new media. With increasing frequency, the spent media is classified a hazardous waste by local regulators. One example of an iron sponge system costs about $50,000 to install with annual operating costs ranging from $250 to $4000.

Proprietary iron-oxide media such as SulfaTreat®, Sulfur-Rite®, and Media-G2® have been installed as improved alternatives to the iron sponge at a few digester sites. These use different media and additional chemical treatment to remove sulfur. Some of these media have limited regeneration capacity or can be deposited in a landfill. One dairy digester site using Media-G2 has two vessels with about 760 kg of media each with a residence time of about 62 seconds per vessel. Annual media consumption ranges from 1460 kg to about 5900 kg with media replacement costs on the order of $2050 to $8290.

Granulated Activated Carbon (GAC) and other carbon media products are used extensively for filtration of contaminants in water and gas streams. GAC contains micropores that capture and hold many organic and polar molecules and is more effective for larger molecules. In other cases, the carbon acts as a catalyst to drive a reaction with the carbon and the selected molecule in a process known as chemisorption.

Commercially available GAC and pelletized activation carbon (PAC) have the surface area in the range of 800-1000 $m^2/g$. These activated carbon media easily adsorb $SO_2$, NOx, and VOCs. The carbon adsorption capacity is dependent on the composition of gas. The $SO_2$ adsorption capacity is about 5-20 grams per 10 g GAC in the dry gas environment.

The GAC adsorbs most VOCs and is used in removing common solvent vapors used in drying cleaning and parts washing operations. The carbon adsorption capacity is strongly dependent on the VOC molecular weight. The adsorption capacities of toluene and methylene chloride at the room temperature are 20 and 5 g/100 g GAC, respectively. However the adsorption capacity of $CH_4$ in GAC is negligible.

Most GAC adsorber systems use two-stage fixed beds. When the first GAC bed is saturated, the GAC is replaced by fresh GAC. Then, the second bed operated as the first bed until GAC is saturated. The saturated GACs are transported to the regeneration plant or disposed in landfill site.

In engine exhaust gas, NOx is present mostly as NO. When the exhaust gas is cooled, NO is converted into $NO_2$. At 60-170° F. the conversion results in equal quantities of NO and $NO_2$. An important aspect of NOx adsorption is that it must be in $NO_2$ form to adsorb on carbon within any reasonable operating temperatures. Therefore, the conversion of NO to $NO_2$ is critical to NOx removal. However, once $NO_2$ is adsorbed in the GAC, it is no longer available in the equilibrium reaction with NO. With sufficient residence time in the GAC, substantially all NO is converted to $NO_2$ and adsorbed in the GAC. Operational experience and laboratory tests show that GAC will adsorb about 10% by weight $NO_2$ in engine exhaust.

The GAC adsorption capacity for $H_2S$ is 5-15% by weight. Therefore, the GAC can be used economically to remove the $H_2S$ from the biogas that contains lower concentrations of $H_2S$. Typically GAC is disposed of in a landfill when saturated with $H_2S$.

Impregnating GAC with alkaline or oxide solids enhance the physical adsorptive characteristics of the carbon with chemical reaction. Sodium hydroxide (NaOH), sodium carbonate ($Na_2CO_3$), and potassium hydroxide (KOH) are common impregnators. The metal oxide impregnation increases the GAC adsorption capacity significantly. Typically, 20-25% loading by weight of $H_2S$ can be achieved, which is 10-15% greater than regular GAC adsorption capacity. The metal-impregnated GAC is almost twice more expensive than GAC. However, the use of metal-impregnated GAC will be more economical for the adsorbers without the on-site carbon reactivation because of its greater adsorption capacity.

Once GAC can no longer adsorb a chemical compound, breakthrough will occur where the contaminant will flow all the way through the bed without being adsorbed. At this point, the GAC is no longer effective and must be replaced. In many cases, such as GAC filled water filters or respirators, the GAC is thrown away and a fresh GAC filter or cartridge is installed. In large scale processes, or where the contaminant can be recovered or destroyed, regeneration of the GAC may be preferred.

There are four processes commonly used for GAC regeneration: Temperature Swing Adsorption (TSA), Pressure Swing Adsorption (PSA) Inert Purge and Displacement Purge. TSA takes place by heating the GAC. With PSA the adsorption takes place at an elevated pressure and regeneration at a lower pressure. Inert gas purge reduces the partial pressure of the adsorbate in the gas phase so that desorption occurs. A purge gas that is more strongly adsorbed than the impurity is used to desorb the original contaminant. Steam regeneration is a combination of TSA and purge. In each process, the contaminant is still present in the purge stream and must be captured, burned or is vented to the atmosphere.

Quantum radiofrequency (RF) physics is based upon the phenomenon of resonant interaction with matter of electromagnetic radiation in the microwave and RF regions since every atom or molecule can absorb, and thus radiate, electromagnetic waves of various wavelengths. The rotational and vibrational frequencies of the electrons represent the most important frequency range. The electromagnetic frequency spectrum is usually divided into ultrasonic, microwave, and optical regions. The microwave region is from 300 megahertz (MHz) to 300 gigahertz (GHz) and encompasses frequencies used for much communication equipment. For instance, refer to Cook, Microwave Principles and Systems, Prentice-Hall, 1986.

Often the term microwaves or microwave energy is applied to a broad range of radiofrequency energies particularly with respect to the common heating frequencies, 915 MHz and 2450 MHz. The former is often employed in industrial heating applications while the latter is the frequency of the common household microwave oven and therefore represents a good frequency to excite water molecules. In this writing the term "microwave" or "microwaves" is generally employed to represent "radiofrequency energies selected from the range of about 500 to 5000 MHz", since in a practical sense this large range is employable for the subject invention.

The absorption of microwaves by the energy bands, particularly the vibrational energy levels, of atoms or molecules results in the thermal activation of the nonplasma material and the excitation of valence electrons. The nonplasma nature of these interactions is important for a separate and distinct form of heating employs plasma formed by arc conditions at a high temperature, often more than 3000.degree. F., and at much reduced pressures or vacuum conditions. For instance, refer to Kirk-Othmer, Encyclopedia of Chemical Technology, 3rd Edition, Supplementary Volume, pages 599-608, Plasma Technology. In microwave technology, as applied in the subject invention, neither of these conditions is present and therefore no plasmas are formed.

Microwaves lower the effective activation energy required for desirable chemical reactions since they can act locally on a microscopic scale by exciting electrons of a group of specific atoms in contrast to normal global heating which raises the bulk temperature. Further this microscopic interaction is favored by polar molecules whose electrons become easily locally excited leading to high chemical activity; however, nonpolar molecules adjacent to such polar molecules are also affected but at a reduced extent. An example is the heating of polar water molecules in a common household microwave oven where the container is of nonpolar material, that is, microwave-passing, and stays relatively cool.

In this sense microwaves are often referred to as a form of catalysis when applied to chemical reaction rates; thus, in this writing the term "microwave catalysis" refers to "the absorption of microwave energy by carbonaceous materials when a simultaneous chemical reaction is occurring" For instance, refer to Kirk-Othmer, Encyclopedia of Chemical Technology, 3rd Edition, Volume 15, pages 494-517, Microwave Technology.

BRIEF SUMMARY OF THE INVENTION

Granulated Activated Carbon (GAC) is placed in adsorbers and used to adsorb hydrogen sulfide ($H_2S$) from the biogas produced in an anaerobic digester. The cleaned biogas is then combusted in a reciprocating engine. The exhaust of the engine is passed through a heat exchanger to cool the exhaust then through adsorbers filled with GAC to adsorb NOx and any remaining sulfur oxides (SOx) or volatile organic carbons (VOC).

The GACs containing NOx, $H_2S$, SOx, and VOCs are transported to a microwave regeneration reactor and exposed to microwave energy. The contaminants desorbed from the GAC are chemically combined into inert nitrogen, water and sulfur. A second microwave reactor filled with GAC reacts any remaining contaminants. A filter removes sulfur from the system.

An embodiment of the invention is an apparatus for decomposing hydrogen sulfide and nitrogen oxides adsorbed in carbon media that comprises a first microwave reactor having a source of microwave energy, where the first microwave reactor is configured to receive a first carbon media containing hydrogen sulfide and nitrogen oxides, a source of sweep gas connected to the first microwave reactor, where hydrogen sulfide and nitrogen oxides are desorbed from the first carbon media in the first microwave reactor when exposed to microwave energy, where the nitrogen oxides react with hydrogen sulfide when exposed to microwave energy to form nitrogen, water and sulfur, and where nitrogen, water and sulfur are removed from the first microwave reactor in the sweep gas.

An aspect of the invention is a second microwave reactor fluidly connected to the first microwave reactor, where the second microwave reactor has a source of microwave energy, a second carbon media positioned in the second reactor, means for filtering sulfur fluidly connected to the second reactor, where the sweep gas flows from the sweep gas source through the first microwave reactor, through the second reactor and through the filtering means.

Another aspect of the invention is where a portion of the hydrogen sulfide is unreacted in the first microwave reactor, where unreacted hydrogen sulfide is transported by the sweep gas from the first microwave reactor to the second microwave reactor, and where hydrogen sulfide is reduced to sulfur and hydrogen when exposed to microwave energy in the second microwave reactor.

A further aspect of the invention is where a portion of the nitrogen oxides are unreacted in the first microwave reactor, where unreacted nitrogen oxides are transported by the sweep gas from the first microwave reactor to the second microwave reactor, and where nitrogen oxides react with the second carbon media to form nitrogen and carbon dioxide when exposed to microwave energy in the second microwave reactor.

A still further aspect of the invention is a biogas adsorber having first carbon media positioned in a biogas stream to adsorb hydrogen sulfide, where the biogas is combusted in an engine, an exhaust gas adsorber positioned in the exhaust stream of the engine, the exhaust gas adsorber having first carbon media to adsorb nitrogen oxides, and where the first carbon media from the biogas adsorber is combined with the first carbon media in the exhaust gas adsorber and positioned in the first microwave reactor.

Another aspect of the invention is where the biogas adsorber is configured as a container to transport first carbon media to the first microwave reactor, and where the exhaust gas adsorber is configured as a container to transport first carbon media to the first microwave reactor.

A further aspect of the invention is a heat exchanger positioned between the engine and the exhaust gas adsorber.

A still further aspect of the invention is where the means for filtering sulfur comprises a particulate filter.

Another embodiment of the invention is an apparatus to remove hydrogen sulfide from biogas and remove nitrogen oxides from the exhaust of an engine fueled by the biogas that comprises a first adsorber having first carbon media configured to remove hydrogen sulfide from a flow of biogas, a second adsorber having first carbon media configured to remove nitrogen oxides from the exhaust of an engine fueled by the biogas, a first microwave reactor configured to receive first carbon media from the first adsorber and the second adsorber, where the first microwave reactor has a source of microwave energy, a source of sweep gas flowing through the first microwave reactor, where hydrogen sulfide and nitrogen oxides are desorbed from the first carbon media in the first microwave reactor when exposed to microwave energy, where the nitrogen oxides react with hydrogen sulfide when exposed to microwave energy in the first microwave reactor to form nitrogen, water and sulfur, and where the nitrogen, water and sulfur flow from the first microwave reactor in the sweep gas.

A further aspect of the invention is a second microwave reactor fluidly coupled to the first microwave reactor, a source of microwave energy coupled to the second microwave reactor, a second carbon media positioned in the second microwave reactor, a particulate filter fluidly connected to the second reactor, where the filter is configured to remove sulfur from the sweep gas, and where the sweep gas flows from the first microwave reactor, through the second reactor and through the filter.

A yet further aspect of the invention is where a portion of the hydrogen sulfide is unreacted in the first microwave reactor, where unreacted hydrogen sulfide is transported by the sweep gas from the first microwave reactor to the second microwave reactor, and where hydrogen sulfide is reduced to sulfur and hydrogen when exposed to microwave energy in the second microwave reactor.

Another aspect of the invention is where a portion of the nitrogen oxides are unreacted in the first microwave reactor, where unreacted nitrogen oxides are transported by the sweep gas from the first microwave reactor to the second microwave reactor, and where nitrogen oxides react with the second carbon media to form nitrogen and carbon dioxide when exposed to microwave energy in the second microwave reactor.

A further embodiment of the invention is a method for removing hydrogen sulfide and nitrogen oxides from carbon media that comprises providing a first microwave reactor adapted to receive first carbon media containing hydrogen sulfide and nitrogen oxides, providing a source of microwave energy in the first reactor, providing a source of sweep gas to the first microwave reactor, positioning first carbon media containing hydrogen sulfide and nitrogen oxides in the first microwave reactor, applying microwave energy to desorb hydrogen sulfide and nitrogen oxides from the first carbon media, reacting the hydrogen sulfide with the nitrogen oxide to form nitrogen, water and sulfur in the first reactor, and transporting nitrogen, water and sulfur from the first microwave reactor in the sweep gas.

Another aspect of the invention is providing a particulate filter fluidly connected to the first microwave reactor, and removing sulfur in the filter.

A further aspect of the invention is providing a second microwave reactor having a source of microwave energy fluidly connected to the first microwave reactor, providing second carbon media in the second reactor, flowing sweep gas from the first microwave reactor, through the second microwave reactor and through the filter.

A still further aspect of the invention is where a portion of the hydrogen sulfide is unreacted, transporting unreacted hydrogen sulfide from the first microwave reactor to the second reactor with the sweep gas, applying microwave energy to the second microwave reactor, and reducing hydrogen sulfide to sulfur and hydrogen in the second reactor.

Another aspect of the invention is where a portion of nitrogen oxides are unreacted, transporting unreacted nitrogen oxides from the first microwave reactor to the second microwave reactor with the sweep gas, applying microwave energy to the second microwave reactor, and combining nitrogen oxides and the second carbon media to form nitrogen and carbon dioxide in the second reactor.

Another embodiment of the invention is a method to remove hydrogen sulfide from biogas and remove nitrogen oxides from the exhaust of an engine fueled by the biogas that comprises providing a first adsorber having first carbon media adapted to remove hydrogen sulfide from a flow of biogas, providing a second adsorber having first carbon media adapted to remove nitrogen oxides from the exhaust of an engine fueled by the biogas, providing a first microwave reactor adapted to receive first carbon media from the first adsorber and the second adsorber, providing a second microwave reactor connected to the first microwave reactor, the second reactor, positioning a second carbon media in the second microwave reactor, providing a filter fluidly connected to the second reactor, providing a sweep gas flowing through the first microwave reactor, the second reactor, and the filter, positioning first carbon media from the first adsorber and the second adsorber in the first microwave reactor, applying microwave energy to the first microwave reactor to remove hydrogen sulfide and nitrogen oxides from the first carbon media, where the nitrogen oxides combine with hydrogen sulfide in the first microwave reactor to form nitrogen, water and sulfur, transporting nitrogen, water and sulfur by the sweep gas from the first microwave reactor to the second reactor, transporting nitrogen, water and sulfur by the sweep gas from the second reactor to the filter, removing sulfur in the filter, and recycling first carbon media from the first microwave reactor to the first and second adsorber.

Another aspect of the invention is where a portion of the hydrogen sulfide is unreacted, transporting unreacted hydrogen sulfide from the first microwave reactor to the second microwave reactor with the sweep gas, applying microwave energy to the second microwave reactor, and reducing hydrogen sulfide to sulfur and hydrogen in the second microwave reactor.

A further aspect of the invention is where a portion of nitrogen oxides are unreacted, transporting unreacted nitrogen oxides from the first microwave reactor to the second microwave reactor with the sweep gas, applying microwave energy to the second microwave reactor, and combining nitrogen oxides and the second carbon media to nitrogen and carbon dioxide in the second reactor.

A yet further aspect of the invention is positioning a heat exchanger between the engine and the exhaust adsorber.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Figure 1:
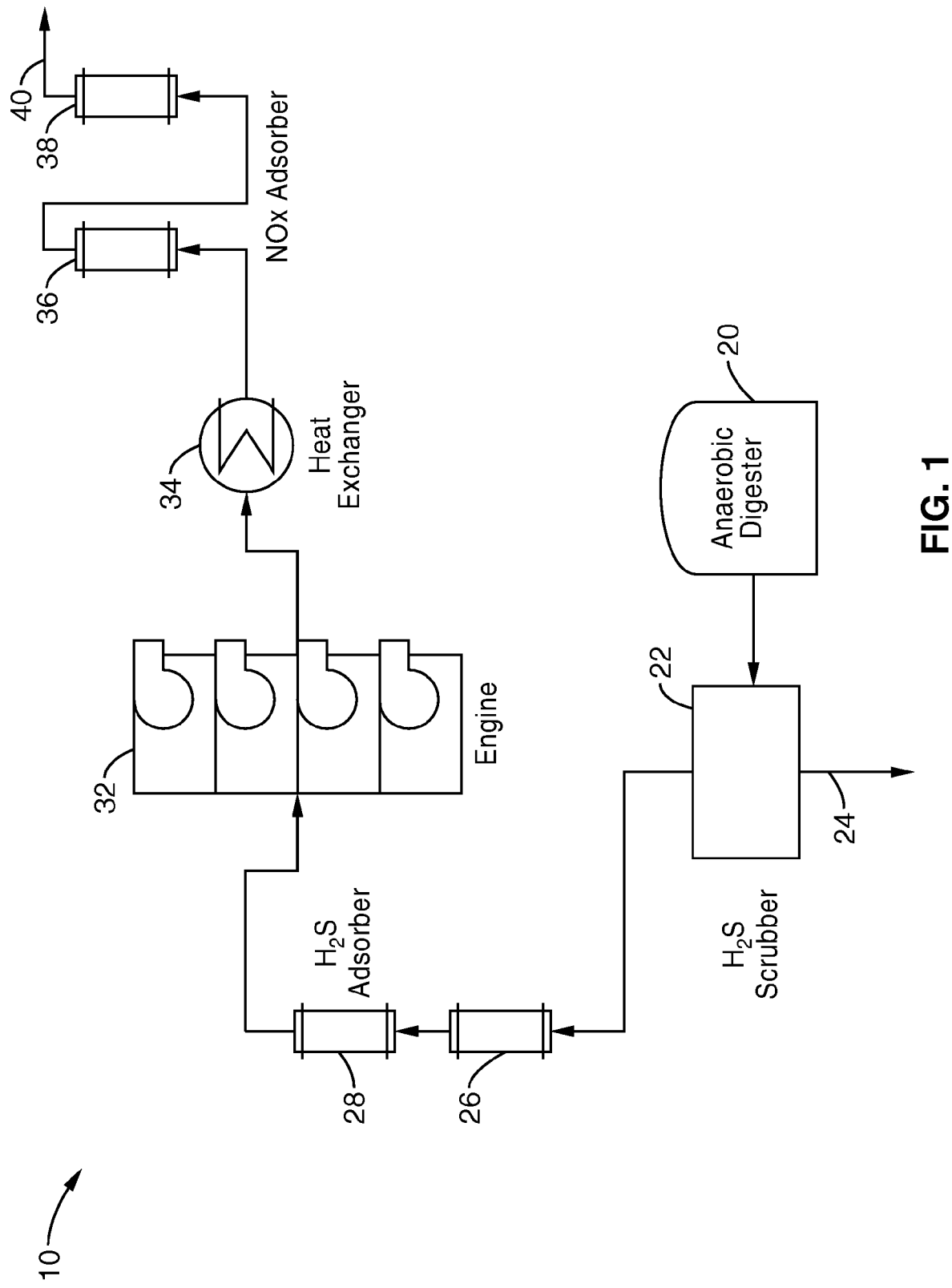
FIG. 1 is a schematic view of a process to remove hydrogen sulfide from biogas and NOx from engine exhaust using carbon media adsorption.
Figure 2:
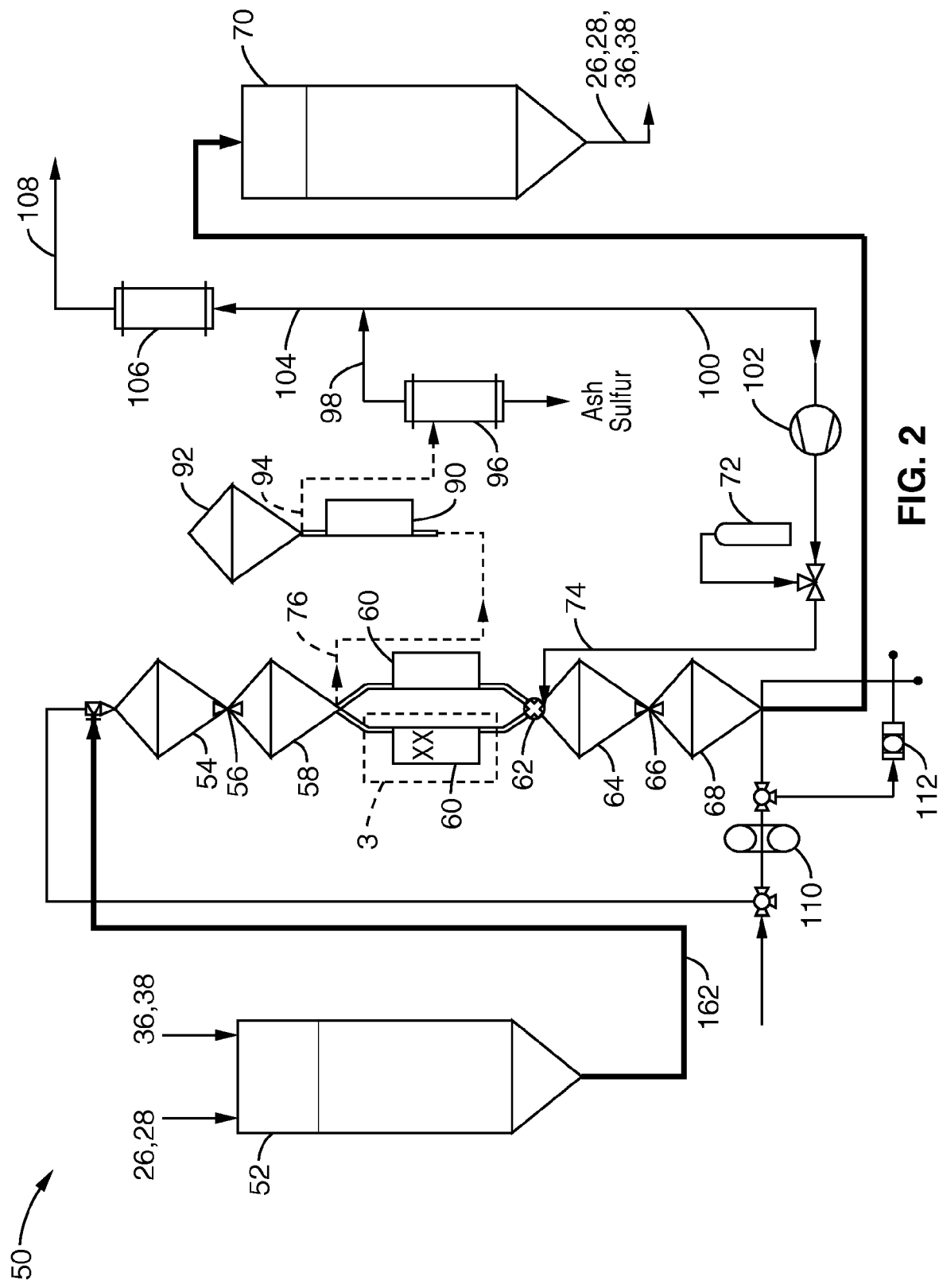
FIG. 2 is a schematic view of an apparatus for removing $H_2S$ and NOx from carbon media with a microwave regeneration system and combining the contaminants to form nitrogen, water and sulfur.
Figure 3:
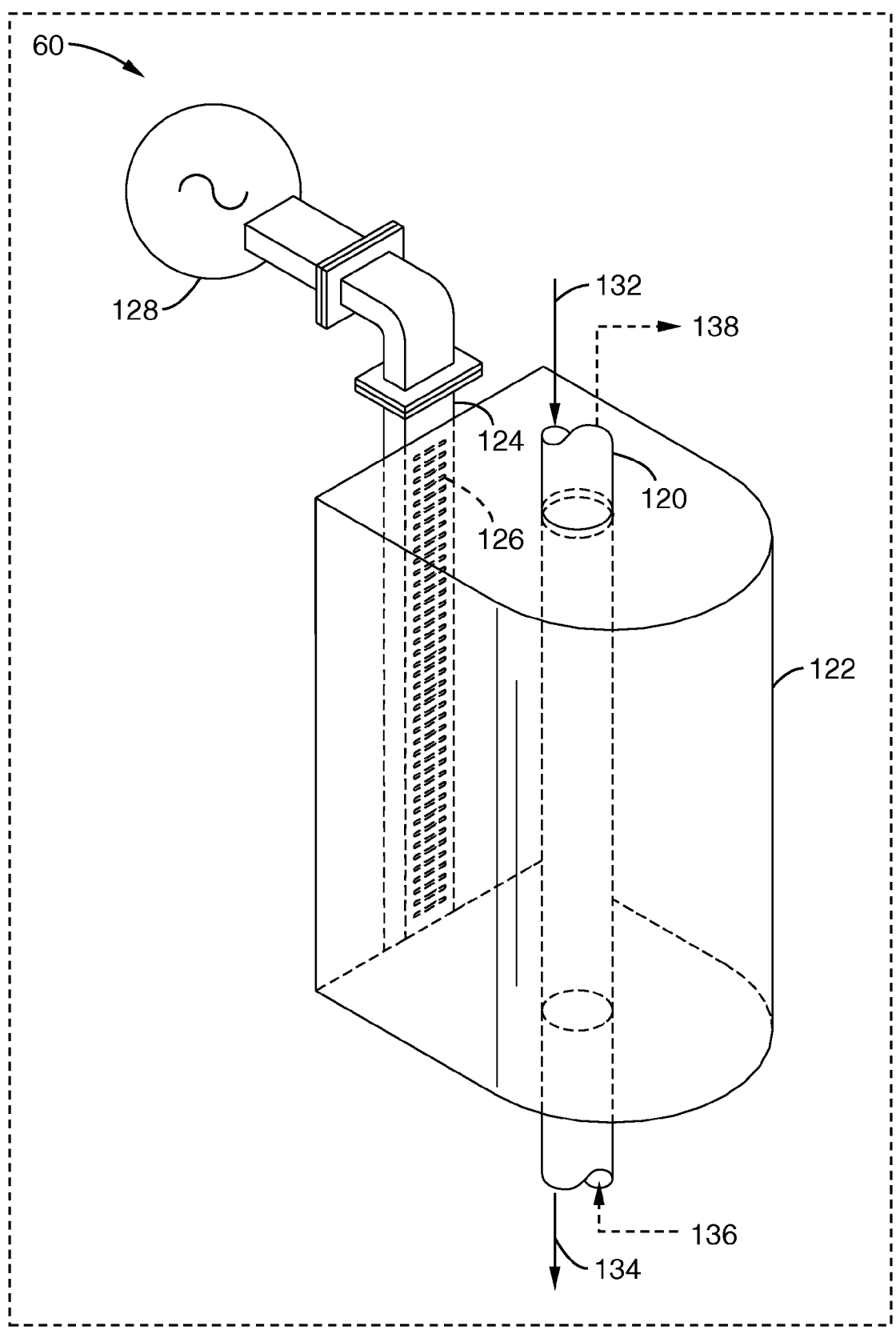
FIG. 3 is a schematic view of an embodiment of a microwave reactor used in the apparatus in FIG. 2.

Referring more specifically to the drawings, for illustrative purposes the present invention is embodied in the apparatus generally shown in FIG. 1 through FIG. 3. It will be appreciated that the apparatus may vary as to configuration and as to details of the parts, and that the method may vary as to the specific steps and sequence, without departing from the basic concepts as disclosed herein.

FIG. 1 is a schematic process diagram of a process 10 for removal of contaminants from the biogas fuel and from the exhaust of the engine running on the biogas. The process takes advantage of the fact that $H_2S$ adsorption capacity of GAC is very close to NOx adsorption capacity. Biogas is generated in an anaerobic animal waste digester 20. Note that the present invention is also applicable to biogas produced in landfills, waster water digesters, and food digesters.

For biogases containing $H_2S$ concentration greater than 1,000-ppm, an iron sponge, bioreactor, or other commercially available $H_2S$ removal system 22 should be installed prior to the GAC adsorber system. The $H_2S$ removal efficiency of the conventional iron sponge system is about 80%. Sulfur waste 24 is typically disposed as a fertilizer or solid waste. The biogas leaving the H₂S scrubber is preferably in the 100 ppm to 500 ppm range but should be below about 1000 ppm. If water condensation in the biogas is a problem, a water knock-out device may be used.

Two adsorbers 26, 28 containing GAC are used to remove remaining H₂S from the biogas. In one mode, the GAC used to remove H₂S from the biogas is the same type of GAC used in the NOx removal system.

The GAC adsorption capacity for H₂S is about 5-10% by weight. If 3,000 lbs GAC adsorbers are used, GAC in the first-stage adsorber needs to be changed every 51 days for 100 kW biogas power generating facility for 1000 ppm H₂S. For a 400 kW biogas generator, the GAC in the first-stage adsorber needs to be changed every 13 days. This carbon change-out schedule is much shorter than the NOx GAC bed change-out schedule and may not be economically feasible for H₂S concentration greater than 1,000-ppm.

KOH-impregnated GAC has H₂S adsorption capacity in the range of 20% to 25%. The increase in the adsorption capacity increases the interval for the carbon change over. For a 100 kW biogas power generating facility, the GAC in the first-stage 3000 lb-adsorber needs to be changed 100 days for biogas containing 1,000-ppm H₂S. For a 400 kW system the GAC change-out needs to be performed every 25 days, within the range of change-out times for a NOx GAC bed. In this example, impregnated GAC is feasible for biogases containing H₂S concentration 1,000-2,000 ppm.

Reciprocating engines 32 are preferred as the generation prime mover because they can tolerate some contamination in the biogas and can operate with higher exhaust backpressure than turbines.

The engine exhaust gas flows into a heat exchanger 34 to recover sensible heat and cool the exhaust prior to entering into the NOx adsorption system. The cooled gas enters adsorber 36 containing the oldest GAC (first-stage adsorber). The gas leaving the first-stage adsorber 36 flows into the second adsorber 38 containing fresh or regenerated GAC (second-stage adsorber). Consequently, whenever the saturated GAC is removed from the first-stage adsorber, the inlet and outlet valves are reversed to change the gas flow direction. As a result, the first-stage adsorber containing regenerated GAC becomes the second-stage adsorber.

The GAC capacity of a typical commercially available adsorber is about 3,000 pounds. For small (50 kW to 400 kW) reciprocating engines, a smaller two-stage vapor GAC adsorber system is used to capture NOx from engine exhaust. A radial adsorber is preferred for higher exhaust flow rates at lower backpressure.

Table 1 is the material balance for an example system as shown in FIG. 1. The basis for the material balance is a 100 kW lean burn engine fed by biogas with a composition of 55% methane, 44% CO₂, and 0.1% H₂S.

The two-stage exhaust GAC adsorption system 36, 38 will remove 99.9% of NOx from the reciprocating engine exhaust. A final NOx concentration of 1 ppm or less is expected in the final exhaust 40. This will meet or exceed California ARB 2007 NOx standards of 0.07 lb/MW-hr for natural gas fired engines. By maintaining a strict GAC change-out schedule, no measurable NOx emission will pass through the second-stage GAC adsorber 38. Note that any SOx produced by engine combustion will also be adsorbed by the GAC and destroyed in the subsequent regeneration process.

Assuming a reciprocating engine producing 2 g/BHP-hr, 10% NOx adsorption capacity and 3,000-lbs GAC adsorbers, the NOx GAC needs to be changed about every 14 days for 400 kW engine and every 56 days for 100 kW engine. Saturated GACs removed from the first-stage adsorber are transported to the central microwave regeneration facility.

FIG. 2 is schematic view of a system and method 50 to remove and destroy H₂S and NOx adsorbed in the GAC using microwave energy.

The GAC containing H₂S and GAC containing NOx is transported to a microwave carbon regeneration facility. These contaminated GACs are mixed and stored in GAC feed tank 52. The mixed GAC is chemically stable and can be stored for an extended period of time.

In one embodiment of the invention, the GAC is transported to the feed hopper 54 of the microwave regeneration system. The mixed GAC in the feed hopper flows downward by gravity to first lock hopper 58 through a valve 56, which prevents air from moving from feed hopper 54 to lock hopper 58. The GAC then flows into the first microwave reactor 60. In this illustration, two parallel reactors 60 are shown to increase media throughput and provide redundancy. Details of an embodiment of microwave reactor 60 are shown in FIG. 3.

Returning to FIG. 2, GAC flows from the feed hopper 58, through first microwave reactor 60, through a rotary feeder valve 62 that regulates the flow and into lower lock hopper 64, through valve 66 and into discharge hopper 64. From there, the media is transported to the regenerated media container 70. Valves 56 and 66 prevent air (with oxygen) from entering microwave reactor 60. Other known systems of transporting the mixed GAC into microwave reactor 60 may be used without the present invention.

A low volume inert sweep gas, such as nitrogen 72, flows in tube 74 into lower lock hopper 64 and in a countercurrent direction through first microwave reactor 60. The mixed GAC in the top hopper flows downward by gravity through the microwave reactor 60. The NOx and H₂S are desorbed rapidly when exposed to microwaves in microwave reactor 60.

As described earlier, NOx are adsorbed onto carbon as NO₂. Since NO₂ is a strong oxidizing agent, the H₂S is oxidized by NO₂ as shown below:

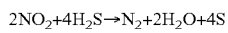

The NO₂ reacts with H₂S at the carbon surface activated with microwave energy to produce N₂, elemental sulfur, and water vapor. These product gases and sulfur are carried out of the first microwave reactor 60 by the low volume sweep gas and into tube 76. At this point, if the reaction of NOx and H₂S is complete, the inert products of reaction may be transported by the sweep gas in tube 76 safely to the environment. Any unreacted NOx or H₂S are also carried out of microwave reactor 60 in the sweep gas.

If a KOH impregnated GAC is used, the H₂S adsorbed onto the KOH-impregnated GAC reacts with KOH at the carbon surface by microwave energy during regeneration as shown below:

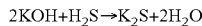

The above reaction illustrates that using regular GAC rather than higher adsorption capacity metal-impregnated GAC will probably be more economical for H₂S removal if combined with GAC adsorption for NOx removal.

The power level and microwave exposure time in reactor 60 is controlled so that any reaction with the GAC is limited. The active pores of the GAC are regenerated by exposure to the microwave energy in microwave reactor 60.

The gas products and sulfur in sweep gas in tube 76 enter into the NOx reduction reactor 90 having a source of microwave energy. NOx reduction reactor 90 is filled with GAC as a reducing agent. Hopper 92 replenishes GAC reacted in NOx reduction reactor 90.

Note that one mole of NOx reacts stoichiometrically with two moles of $H_2S$. If the $H_2S$ desorbed from GAC in microwave reactor 60 is not sufficient to consume all NOx desorbed from GAC, unreacted NOx will be transported by the sweep gas to the NOx reduction reactor 90. NOx reacts with carbon in the presence of microwave energy to form Nitrogen ($N_2$) and Carbon Dioxide ($CO_2$). as shown below:

$$2NO+C \rightarrow N_2+CO_2$$

$$2NO_2+2C \rightarrow N_2+2CO_2$$

One mole of carbon will be consumed for each mole of NOx reacted. This carbon will also react with any SOx that may have been adsorbed in the exhaust gas GAC to form sulfur and $CO_2$.

However, if the moles of $H_2S$ desorbed from GAC in microwave reactor 60 are greater than twice of the moles of NOx desorbed, the remaining $H_2S$ will flow in the sweep gas in tube 76 to NOx reduction reactor 90.

$H_2S$ is reduced to $H_2$ gas and elemental sulfur at the carbon surface in the NOx destruction reactor 90 when exposed to microwave energy. This situation is very unlikely, however, because the $H_2S$ moles are not expected to be greater than twice of $NO_2$ moles in the NOx reduction reactor 90.

The carbon in the NOx reduction reactor 90 is an excellent microwave energy absorber and also strong reducing agent. The $NO_2$ reacts with carbon rapidly with microwave energy. Since $NO_2$ is a powerful oxidizing agent, the destruction efficiency for the desorbed $H_2S$ will be greater than 99%. Furthermore, the carbon is a strong reducing agent that reduces $H_2S$ into the elemental sulfur and hydrogen gas. Based on operational experience with existing microwave treatment systems, the emissions from the treatment system are expected to be less than 1 ppm for NOx, SOx, and CO.

Note that the carbon in the NOx reduction reactor 90 is consumed by excess NOx and can be composed of lower quality carbon materials such as coal char or previously used GAC with non-volatile contaminants. An example would be used GAC from water filtration.

The sweep gas and particulate sulfur flows out from the NOx reduction microwave reactor 90 through tube 94 and enters into a particulate filter 96 that captures the elemental sulfur and remaining ash from GAC consumption. In one embodiment, particulate filter 96 is a cleanable or vibrating filter. A cyclone may also be integrated into particulate filter 96. The sweep gas entering filter 96 may also be cooled to increase filter efficiency. The filtered sweep gas is now clean gas consisting mostly of nitrogen, $H_2O$, and $CO_2$.

Some of the clean gas leaving filter 96 is recycled back through the regeneration reactor 60 through tube 100 and compressor 102 connected to tube 74. Any excess clean gas is vented through tube 104. In one mode, a GAC filter 106 is used before the clean gas is vented to the atmosphere at vent 108.

The regenerated GAC that passed through first microwave reactor 60 is transported from discharge hopper 68 to the regenerated GAC storage tank 70. In one embodiment, a pneumatic blower 110 is used to transport the GAC through the system. A particulate filter 112 is used to filter out carbon fines from handling and transporting the GAC. Alternatively, a mechanical transport system is used to transport the carbon media.

The pores in the regenerated media are reactivated by the exposure to microwave energy in microwave reactor 60 and typically have the same or better adsorption capacity as new media. The regenerated media in storage tank 70 is transported back to the adsorption vessels 26, 28, shown in FIG. 1 to further clean the biogas and to adsorption vessels 36, 38 to remove NOx from engine exhaust. Depending on attrition due to reaction or handling, new GAC is added to regenerated media storage tank 70.

Table 2 is a material balance for an example system as shown in FIG. 2. The basis for this material balance is a carbon regeneration system capable of processing 100 lb of GAC per hour. The ratio of $H_2S$ and NOx saturated GAC was determined from the material balance presented in Table 1. In that case, $H_2S$ reacts completely with the $NO_2$ present, and the excess $NO_2$ reacts with GAC in the microwave reactor to produce inert $CO_2$ and $N_2$.

In one mode, the microwave GAC regeneration facility can be constructed on a trailer. This portable microwave unit can be transported to the power producing site to avoid difficulties associated with transporting saturated GAC.

The advantages of the on-site GAC regeneration system are: (1) eliminate transportation of GAC from the biogas generation site to the central regeneration facility; (2) GAC is not removed from the treatment system, eliminating any difficulty involved in the GAC change-out; and handling of GAC. The on-site GAC regeneration system cost decreases as the power generating capacity or biogas flow rate increases. Consequently, the on-site regeneration will be the best for larger systems such as a 400 kW power producing dairy farm.

For an area where many 400 kW or smaller biogas power generation facilities are located within a relatively short distance, it may be more cost-effective to build a central microwave regeneration facility. If the adsorbers are relatively small and portable, when GAC in the first stage adsorbers (26, 36 in FIG. 1) are saturated, the adsorbers are disconnected from the adsorption system. These used adsorbers are replaced by adsorbers filled with regenerated GAC. The used adsorbers are transported to the central microwave regeneration facility and the saturated GAC is regenerated in the microwave reactor. If large adsorbers are used for $H_2S$ and NOx abatement, saturated GAC is removed from the adsorber and replaced by regenerated GAC and the removed GAC is transported to the central regeneration facility and regenerated.

FIG. 3 is a schematic view of a microwave reactor 60 shown in FIG. 2. A tube 120, which is transparent to microwave energy, is positioned in microwave cavity 122. Microwave cavity 122 will contain microwave energy and, in this example, is shaped similar to a rural mailbox. In one embodiment, tube 120 is quartz glass and about 4 inches in diameter to provide good microwave penetration to media in the center of the tube.

A rectangular wave guide 124 is attached to microwave cavity 122 and communicated energy through a row of slots 126. The width of the slot and spacing is optimized for microwave energy. A source of microwave energy 128 is attached to waveguide 124.

Contaminated media enters tube 120 at media inlet 132 and flow downward through the microwave field and exits at media outlet 134. Sweep gas enters at the bottom of the reactor at gas inlet 136 and flows upward through tube 120 and out at gas outlet 138. When exposed to microwave energy, gaseous contaminants are quickly desorbed from the media in tube 120 and removed in the sweep gas.

In another embodiment of the invention, microwave cavity 122 is water-cooled. In a further embodiment, microwave cavity 122 is air-cooled.

NOx destruction microwave reactor 90, shown in FIG. 2, is of similar design as the reactor shown in FIG. 3. In one embodiment, microwave reactor 60 and NOx destruction microwave reactor 90 share the same source of microwave energy.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Material Balance for $H_2S$ and NOx Removal System

| Stream | CH4 (lb/hr) | N2 (lb/hr) | O2 (lb/hr) | CO2 (lb/hr) | H2O (lb/hr) | H2S (lb/hr) | NO (lb/hr) | NO2 (lb/hr) |
|---|---|---|---|---|---|---|---|---|
| 20 | 73.1 | 0 | 0 | 162 | 0 | 2.26 | 0 | 0 |
| 22 | 73.1 | 0 | 0 | 162 | 0 | 1.41E−01 | 0 | 0 |
| 26 | 73.1 | 0 | 0 | 162 | 0 | 1.41E−02 | 0 | 0 |
| 28 | 73.1 | 0 | 0 | 162 | 0 | 1.41E−03 | 0 | 0 |
| 32 | 0 | 2925 | 263 | 363 | 165 | 0 | 2.96E−01 | 3.29E−02 |
| 34 | 0 | 2925 | 263 | 363 | 165 | 0 | 1.64E−01 | 1.64E−01 |
| 36 | 0 | 2925 | 263 | 363 | 165 | 0 | 1.64E−02 | 1.64E−02 |
| 38 | 0 | 2925 | 263 | 363 | 165 | 0 | 1.64E−03 | 1.64E−03 |

TABLE 2

Microwave Regenerator Material Balance

| | GAC(lb/hr) | NO2 (lb/hr) | H2S (lb/hr) | N2 (lb/hr) | S (lb/hr) | CO2 (lb/hr) | H2O (lb/hr) | Ash (lb/hr) |
|---|---|---|---|---|---|---|---|---|
| Carbon Inlet | 100 | 7.44 | 3.20 | 0 | 0 | 0 | 0 | 0 |
| Regenerated Carbon | 99.0 | 0 | 0 | 0 | 0 | 0 | 0 | 0 |
| Recycled Sweep Gas | 0 | 0 | 0 | 9.36 | 0 | 1.47 | 0.493 | 0 |
| Saturated Sweep Gas | 0 | 7.44 | 3.20 | 9.36 | 0 | 1.47 | 0.493 | 0 |
| Reacted Sweep Gas | 0 | 0 | 0 | 11.6 | 3.01 | 5.05 | 1.69 | 0.250 |
| Ash-Free Sweep Gas | 0 | 0 | 0 | 11.6 | 0 | 5.05 | 1.69 | 0 |
| Ash Outlet | 0 | 0 | 0 | 0 | 3.01 | 0 | 0 | 0.250 |
| Reactor Makeup Carbon | 2.09 | 0 | 0 | 0 | 0 | 0 | 0 | 0 |
| Sweep Gas Purge | 0 | 0 | 0 | 8.24 | 0 | 3.58 | 1.20 | 0 |
| Vent to Atmosphere | 0 | 0 | 0 | 8.24 | 0 | 3.58 | 1.20 | 0 |
| Nitrogen Supply | 0 | 0 | 0 | 4.27 | 0 | 0 | 0 | 0 |

What is claimed is:

1. A method for removing hydrogen sulfide and nitrogen oxides from carbon media, comprising:

providing a first microwave reactor adapted to receive first carbon media containing hydrogen sulfide and nitrogen oxides;

providing a source of microwave energy in said first reactor;

providing a source of sweep gas to said first microwave reactor;

positioning first carbon media containing hydrogen sulfide and nitrogen oxides in said first microwave reactor;

applying microwave energy to desorb hydrogen sulfide and nitrogen oxides from said first carbon media;

reacting said hydrogen sulfide with said nitrogen oxide to form nitrogen, water and sulfur in said first reactor; and transporting nitrogen, water and sulfur from said first microwave reactor in said sweep gas.

2. A method as recited in claim 1, further comprising:

providing a particulate filter fluidly connected to said first microwave reactor; and removing sulfur in said filter.

3. A method as recited in claim 2, further comprising:

providing a second microwave reactor having a source of microwave energy fluidly connected to said first microwave reactor;

providing second carbon media in said second reactor;

flowing sweep gas from said first microwave reactor, through said second microwave reactor and through said filter.

4. A method as recited in claim 3, further comprising:

wherein a portion of said hydrogen sulfide is unreacted;

transporting unreacted hydrogen sulfide from said first microwave reactor to said second reactor with said sweep gas;

applying microwave energy to said second microwave reactor, and reducing hydrogen sulfide to sulfur and hydrogen in said second reactor.

5. A method as recited in claim 3, further comprising:

wherein a portion of nitrogen oxides are unreacted;

transporting unreacted nitrogen oxides from said first microwave reactor to said second microwave reactor with said sweep gas;

applying microwave energy to said second microwave reactor, and combining nitrogen oxides and said second carbon media to form nitrogen and carbon dioxide in said second reactor.

6. A method to remove hydrogen sulfide from biogas and remove nitrogen oxides from the exhaust of an engine fueled by the biogas comprising:

providing a first adsorber having first carbon media configured to remove hydrogen sulfide from a flow of biogas;

providing a second adsorber having first carbon media configured to remove nitrogen oxides from the exhaust of an engine fueled by said biogas;

providing a first microwave reactor configured to receive first carbon media from said first adsorber and said second adsorber;

providing a sweep gas source fluidly connected to said first microwave reactor;

wherein sweep gas flows from said sweep gas source through said first microwave reactor;

combining first carbon media from said first adsorber with first carbon media from said second adsorber in said first microwave reactor;

applying microwave energy to said first microwave reactor to remove hydrogen sulfide and nitrogen oxides from said first carbon media;

wherein said nitrogen oxides combine with hydrogen sulfide in said first microwave reactor to form nitrogen, water and sulfur;

transporting nitrogen, water and sulfur from said first microwave reactor in said sweep gas; and transporting said first carbon media from said first microwave reactor to said first adsorber and said second adsorber.

7. A method as recited in claim 6, further comprising:

providing a second microwave reactor fluidly connected to said first microwave reactor, positioning a second carbon media in said second microwave reactor;

providing a filter fluidly connected to said second reactor;

wherein sweep gas flows from said sweep gas source, through said first microwave reactor, through said second microwave reactor and through said filter;

transporting nitrogen, water and sulfur by said sweep gas from said first microwave reactor to said second reactor;

transporting nitrogen, water and sulfur by said sweep gas from said second reactor to said filter; and removing sulfur in said filter.

8. A method as recited in claim 7, further comprising:

wherein a portion of said hydrogen sulfide is unreacted;

transporting unreacted hydrogen sulfide from said first microwave reactor to said second microwave reactor with said sweep gas;

applying microwave energy to said second microwave reactor, and reducing hydrogen sulfide to sulfur and hydrogen in said second microwave reactor.

9. A method as recited in claim 7, further comprising:

wherein a portion of nitrogen oxides are unreacted;

transporting unreacted nitrogen oxides from said first microwave reactor to said second microwave reactor with said sweep gas;

applying microwave energy to said second microwave reactor, and combining nitrogen oxides and said second carbon media to nitrogen and carbon dioxide in said second reactor.

10. A method as recited in claim 6, further comprising positioning a heat exchanger between said engine and said exhaust adsorber.

* * * * *